United States Patent [19]

Kasahara et al.

[11] Patent Number: 4,988,183
[45] Date of Patent: Jan. 29, 1991

[54] EYE MOVEMENT INSPECTION DEVICE

[75] Inventors: Tatsuya Kasahara, Amagasaki; Kyuichi Kishi, Kobe, both of Japan

[73] Assignee: Konan Camera Research Institute, Inc., Hyogo, Japan

[21] Appl. No.: 365,189

[22] Filed: Jun. 12, 1989

[30] Foreign Application Priority Data

Jun. 13, 1988 [JP] Japan .................................. 63-145425

[51] Int. Cl.⁵ .............................................. A61B 3/14
[52] U.S. Cl. .................................. 351/210; 351/206; 351/158
[58] Field of Search ............... 351/209, 210, 158, 206; 2/426

[56] References Cited

U.S. PATENT DOCUMENTS 4,702,575 10/1987 Breglia ................................. 351/210
4,815,839 3/1989 Waldorf ............................... 351/210
4,838,681 6/1989 Pavlidis .............................. 351/210

Primary Examiner—Rodney B. Bovernick
Attorney, Agent, or Firm—Koda and Androlia

[57] ABSTRACT

An eye movement inspection device of goggle shape with a light-shut-out cover which creates a "dark room" in front of eyes. Inside of the goggles, infrared ray radiators (LEDs) illuminate light on the eyes through reflection plates, and micro TV camera catch eye movement which is made when the eyes follow the on-and-off target LEDs arranged in cross shape in front of the eyes. The infrared ray radiator, TV camera, reflection plates and target LEDs are assembled in a single unit, forming a movable eyepiece for each eye, and the eyepieces provided side by side are freely movable horizontally, vertically and in the direction of ocular axis.

11 Claims, 4 Drawing Sheets

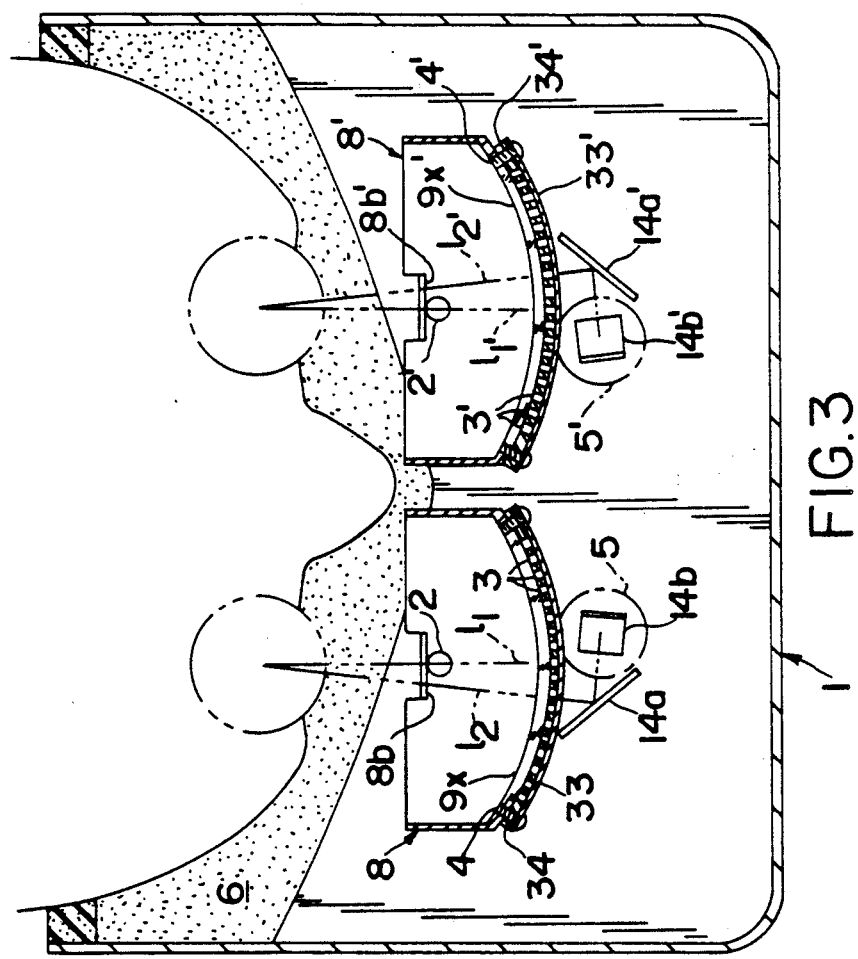
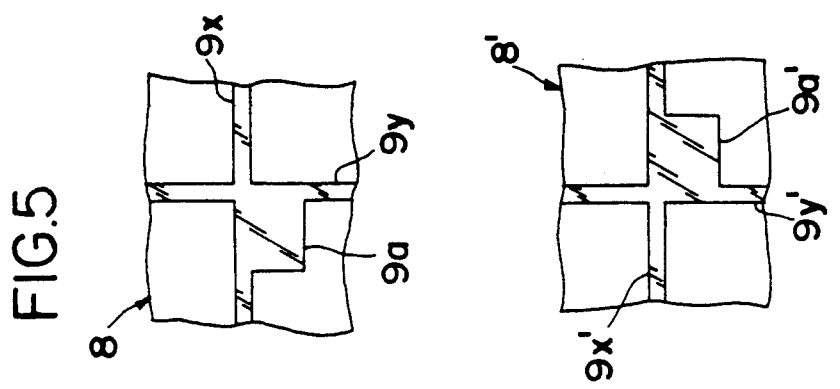

EYE MOVEMENT INSPECTION DEVICE

BACKGROUND OF THE INVENTION

1. Field of the Invention

The present invention relates to an optical vision device used in medical diagnosis, and more particularly to a inspection device for observing, recording and analyzing the eyes of patients by detecting vertical, horizontal and rotational eye movements.

2. Prior Art

Observation of a patient's eye movements is an indispensable diagnostic tool for clinical investigation of inner-ear, balance and central nerve dysfunction. Dizziness and disorders of these systems have a recognized relationship, and by testing the eye movements of a patient, symptoms of such disorders can be found. Thus, a variety of eye movement detecting devices are widely used.

As ordinary inspection devices, there are so-called "ENG" and "EOG" devices which utilize characteristic differences in the electrical potential between the cornea and retina. In such devices, electrodes are set on the surface of the skin near the eye sockets so that the electrical potential difference created by eye movements is collected and recorded through the electrodes. In the ENG device, such difference is outputted as an alternating current so that eye movement velocity is recognized, and in the EOG device, the differences are outputted as a direct current so as to indicate eye movement fluctuations.

In another device called a "PRNG," an infrared ray is radiated to the right and left sides of the eyeballs, and the intensity of light reflected on the cornea and retina is observed and then the eye movements are recorded on a polygraph. Another device which private practitioners often use is a Franzel lens device. In this device, eye movements are directly observed via a 20 diopter lens equipped with a light source. Recently, such a device is sold with a TV camera attached.

In addition, there is another device defined as a "search coil." In this device, a patient wears contact lenses having coils therein, and eye movement signals are outputted via a magnetic field device. In a recently developed device, an infrared ray TV camera catches reflected light from the infrared ray radiation from the eyes to obtain signals of eye movement through the camera. Devices of this type are disclosed in publications such as Ann Otol Phinol Laryngol, 1977 and Acta Otolarygol, 1987.

However, tests conducted with the ENG and EOG devices are likely to be affected by noise caused by the electrical potential of the skin, since the electrical potential of the cornea-retina and skin are the same. Also, in such devices, fluctuations in potentials often result, and unless the vertical and horizontal lead lines from the electrodes on the skin are crossed at completely right angles, fluctuations can easily occur thus decreasing the accurate detection. Moreover, cycloduction movement of the eyeballs cannot be tested, and also the test must be performed in a dark room. Furthermore, since the electrical potential of the cornea and retina are unsteady, frequent corrections and adjustments are required. In addition, ENG and EOG devices are easily affected by blinking and movements of the eyelids, and when eyes are closed to avoid visual fixation (involuntary viewing at one position), vertical eye vibrations (eye movement in the vertical direction) occurs, and therefore, true eye movement cannot be observed. Also, since a separate target display is necessary to conduct tests with these devices, a fairly large space is required.

A test with the PENG device is likely to be affected by blinking or eyelid movements, and since the test must be performed while the eyes are open, visual fixation can easily occur and nystagmus (eyeball movement) may be lowered. Although there is no affect from the electrical potential of the skin, the test must be conducted in a dark room, as in the case of ENG and EOG devices, and a separate target display is still required. Furthermore, the cycloduction movement cannot be tested either.

With the Franzel lens device, cycloduction can be confirmed visually, and the test can be performed in a lighted room. However, the eyes cannot follow a moving display target, and visual fixation cannot be completely eliminated. Besides these disadvantages, it is impossible to obtain continuous recording and analysis of the reactions of eye movements with this device.

The "search coil device" requires that patients wear contact lenses, and the test must be done inside a magnetic-field device. Accordingly, patient's movement tends to be minimal, and natural eye movement cannot be observed. In addition, devices which use reflected light caused by radiation of infrared ray, as disclosed in the noted publications, require dark rooms, and complicating testing procedure.

SUMMARY OF THE INVENTION

With the above-described disadvantages of the prior art in mind, it is a primary object of the present invention to provide an eye movement inspection device wherein tests can be performed without affecting the electrical potential of the skin, wherein a large space is not required for the patient to freely move during the test without restricting the patient's head movement, wherein visual fixation can be eliminated, and vertical, horizontal and rotational eye movements are accurately tested in a lighted room so that the test results can be used to observe, record and analyze movement of the eyes.

It is another object of the present invention to provide an eye movement inspection device which is provided with built-in testing targets so that a large space for setting up a target display is no longer necessary.

It is still another object of the present invention to provide an eye movement inspection device wherein both eyes may be simultaneously observed, and wherein the parts of the device are easily adjusted so that the device can be accurately fitted on patients despite the differences in the conditions of each patient's eyes such as distance between the eyes, etc.

In order to accomplish the objects, the device of the present invention creates a "darkroom" in front of the patient's eyes using goggles which have a flexible light shutter fitting on the face and head of the patient to shut out visible light entering the patient's eyes. The goggles are designed to be mountable on the patient's head so that the patient can freely move any ways with the goggles on.

Furthermore, inside the goggles, infrared ray radiators are provided so that light can be radiated onto the patient's eyes, and infrared ray detecting TV cameras are provided in the goggles so that the optical axes of the camera face the eyes of the patient and the infrared ray image of the patient's eye movement is obtained, whereby image signals are outputted from the cameras to be used in the tests.

It is preferable to provide reflector in the goggles so that reflection plates reflect and disperse the infrared ray to illuminate the patient's eyes. It is also preferable to provide viewing targets of visible-light sources emitting visible light onto the eyeballs.

In addition, so as to correspond to the left and right eyes of a patient, the infrared ray radiator, infrared ray detecting TV camera, reflection plates and viewing target are assembled in a single unit so that two units make a pair of mobile eyepieces in the goggles. The eyepieces are freely movable horizontally, vertically and in the direction of ocular axis so that the optical axes of the TV cameras of the respective mobile eyepieces are adjusted via an optical axis adjustment device and that the optical axes of the TV cameras can properly face the eyes.

An infrared ray emitting LED is suitable for the infrared ray radiator. For the viewing targets, a plurality of visible-light emitting diodes (LEDs) having a variable display functions are arranged on a spherical surface which is centered at the center of eye movement. The viewing targets are arranged in cross shape, vertically and horizontally, with the intersection of LEDs on an ocular axis on a reflection plate of a prescribed shape having a spherical reflection surface. The optical axis of the TV camera is positioned in proximity to such intersection targets and passes through the reflection plate. In order to easily mount the goggles, an air band is used.

With the above described structure, when the eye movement inspection device is placed on a patient, the shutter of the goggles create a "darkroom" in front of the patient's eyes, and the infrared ray from the infrared ray radiator (such as an infrared LED) is reflected and dispersed by the reflection plates and irradiated onto the eyes so that image signals of the patient's eye movements are collected through the infrared ray detecting TV cameras.

Because of the "dark room" created in front of the eyes, visual fixation is eliminated, and because the goggles can move along with the patient's head, free movement of the patient's head is enhanced. Consequently, a test of free eye movement can be accomplished, and observation, recordation and analysis of eye movement including cycloduction are executed through the image signals caused by such eye movement.

In addition, according to the present invention, because of the goggles, it is not necessary to perform the test in dark room. Also, since the viewing targets consisting of visible-light sources are provided in the goggles, a large space for setting-up a target display is not necessary. Furthermore, since multiple targets are arranged on a spherical surface which is parallel to eye movement, eye movement is observed accurately without adjusting positions of the target display.

Moreover, the infrared ray radiator, infrared ray detecting TV camera, reflection plates and viewing targets are assembled in a single unit, and two such units are provided in the goggles to form a pair of mobile eyepieces to facilitate simultaneous observation of both eyes. Since the pair of mobile eyepieces are adjustable via an optical axis adjustment device in the vertical direction, horizontal direction (which is the direction of the width of the eye and in the direction of ocular axis), accurate tests of eye movements are possible despite differences in eye positions of individuals. Furthermore, with the air band provided on the goggles, it is very easy to put the goggles on the patient.

BRIEF DESCRIPTION OF THE DRAWINGS

FIG. 3 is a cross sectional view taken along the line B—B of FIG. 1;

FIG 5 is a partial rear view of a central transparent window of a right side eye cap used in the inspection device; and FIG. 6 is a partial rear view of a central transparent window of a left side eye cap used in the inspection device.

DETAILED DESCRIPTION OF THE INVENTION

Figure 1:
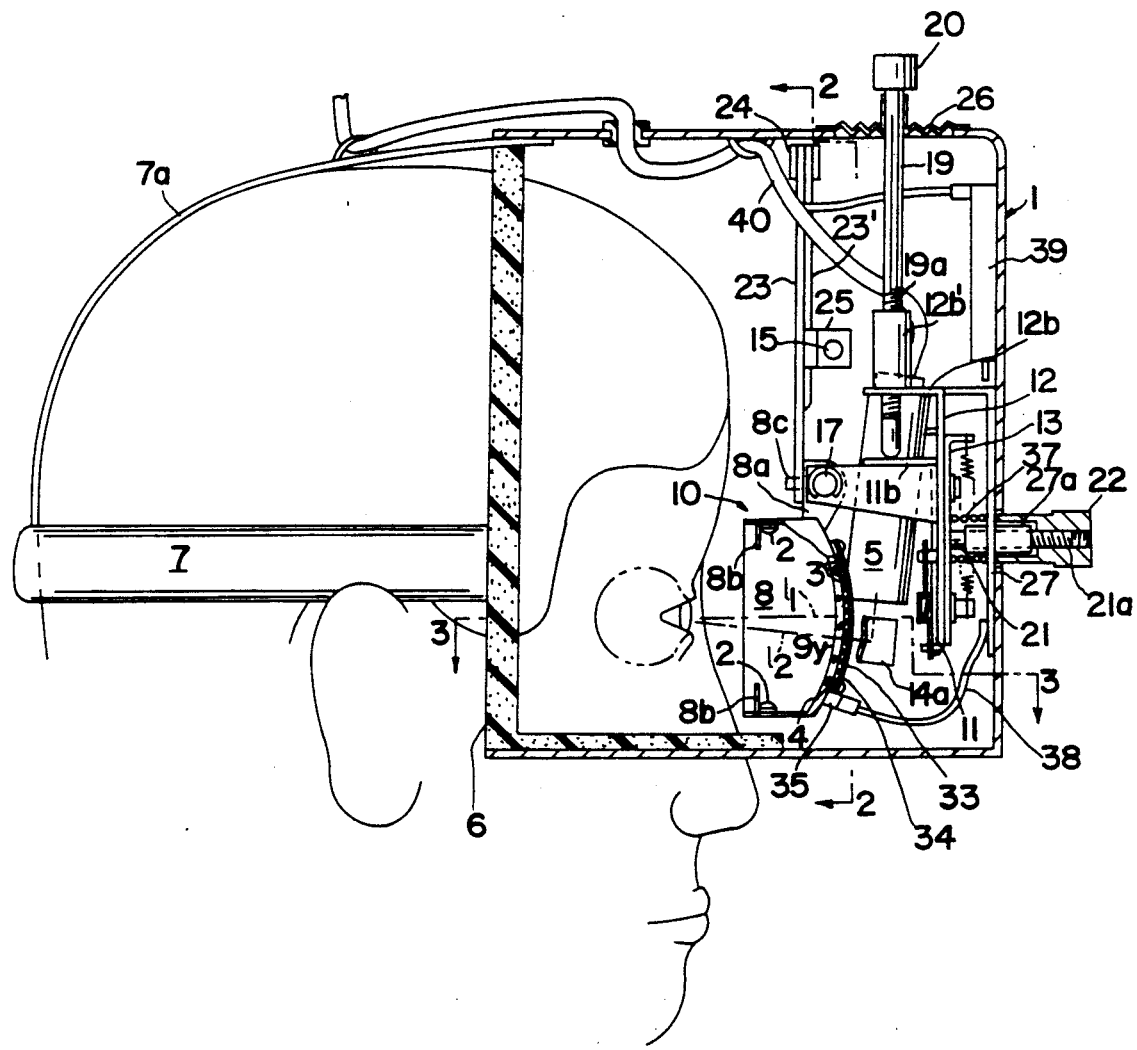
FIG. 1 is a side, cross sectional view of the eye movement inspection device of the present invention placed on a patient.

In Figures, goggles 1 are made of a light alloy or polyester containing glass fibers and are designed so that when mounted on a patient they create a "darkroom" in front of the eyes of the patient. More particularly, the goggles 1 are in a box shape so that there are a pair of eye cap shaped mobile eyepieces 10 and 10' therein which are used for executing eye movement observation as described below. Along the area where the goggles 1 are in contact with the patient's face, a shutter assembly 6 consisting of flexible materials (such as urethane foam) which serve to shut out light is provided over the goggles so that they snugly fit on the patient's face.

At the right and left sides of the goggles 1 which come in contact with the patient's face, an air band 7 is attached which can expand when air is supplied thereto at a predetermined pressure, thus securing the goggles 1 on the patient. The air band 7 has a head band 7a which comes on top of the patient's head. The air band 7 expands under pressure by compressed air sent from an air pump (not shown) so that the goggles 1 fit securely on the patient and can be easily removed by reducing the air pressure. The pressure is always kept at the same level so that the goggles 1 can be worn any patient.

Corresponding to both right and left eyes of the patient, a pair of mobile eyepieces 10 and 10' that detect the infrared images of the eyes upon radiation of infrared ray, are provided inside the goggles 1 in a floating manner. That is, the eyepieces 10 and 10' are provided adjustable in mutual spacing, any of X direction (horizontal), Y direction (vertical) and Z direction (ocular axis direction).

The mobile eyepieces 10 and 10' are equipped with eye caps 8 and 8' that function as reflection plates. The eye caps 8 and 8' are incorporated with infrared ray diodes (IR-LEDs) 2 and 2' which radiate infrared rays to the eyes of the patient and reflection plates 4 and 4' which reflect and disperse the infrared rays coming from the diodes (LEDs) 2 and 2' to flash over the eyes of the patient. A group of targets 3 and 3' consisting of LEDs radiating visible light onto the patient's eyes are also provided in the eye caps 8 and 8'. In addition, ultra-miniature, infrared ray detecting TV cameras 5 and 5' equipped with CCDs for detecting infrared images of the patient's eyes are provided in the goggles 1 along with two mirrors which reflect optical axes.

The eye caps 8 and 8' are in a box shape provided with reflection plates 4 and 4' which have spherical inner reflection surfaces. Each of the reflection surfaces is centered at essentially the rotating center of the eyeball. In other words, each of the reflection surfaces is parallel to the movement of the eye. On the front, inner surfaces of the flat upper and lower walls of the eye caps 8 and 8' are provided with infrared ray luminous diodes (IR-LEDs) 2 and 2' so that they are located in front of vertical walls 8b and 8b' of the upper and lower walls which are above and beneath the ocular-axes of the eyes (wiring for the LEDs is omitted in the drawings).

The reflection plates 4 and 4' have coatings on the reflecting surfaces, and a plurality of (target LEDs) LEDs 3 and 3' are provided thereon. The LEDs 3 and 3' are arranged in a cross shape pattern with one target LED at the center located essentially on the ocular axes 11 and 11'. These LEDs 3 and 3' form a viewing target group and provided on flexible substrates 33 and 33' through supporting pieces 34 and 34' and behind the cross shaped transparent window 9x and 9y and 9x' and 9y' of the reflection plates 4 and 4' (FIGS. 1, 3 and 5).

Near the target LED at the intersection of the LEDs arranged in cross shape in the target group 3 and 3' and on optical paths of the infrared image of the eyes, predetermined rectangular shaped transparent windows 9a and 9a' are provided. As seen from FIGS. 5 and 6, the windows 9a and 9a' are provided along the X direction (horizontal) transparent windows 9x and 9x' and Y direction (vertical) transparent windows 9y and 9y' of the cross shaped transparent windows; and in the left side eye cap 8, the transparent window 9a is at the lower left side of the cross (FIG. 5), and in the right side eye cap 8' the transparent window 9a' is at the lower right side of the cross (FIG. 6).

Figure 2:
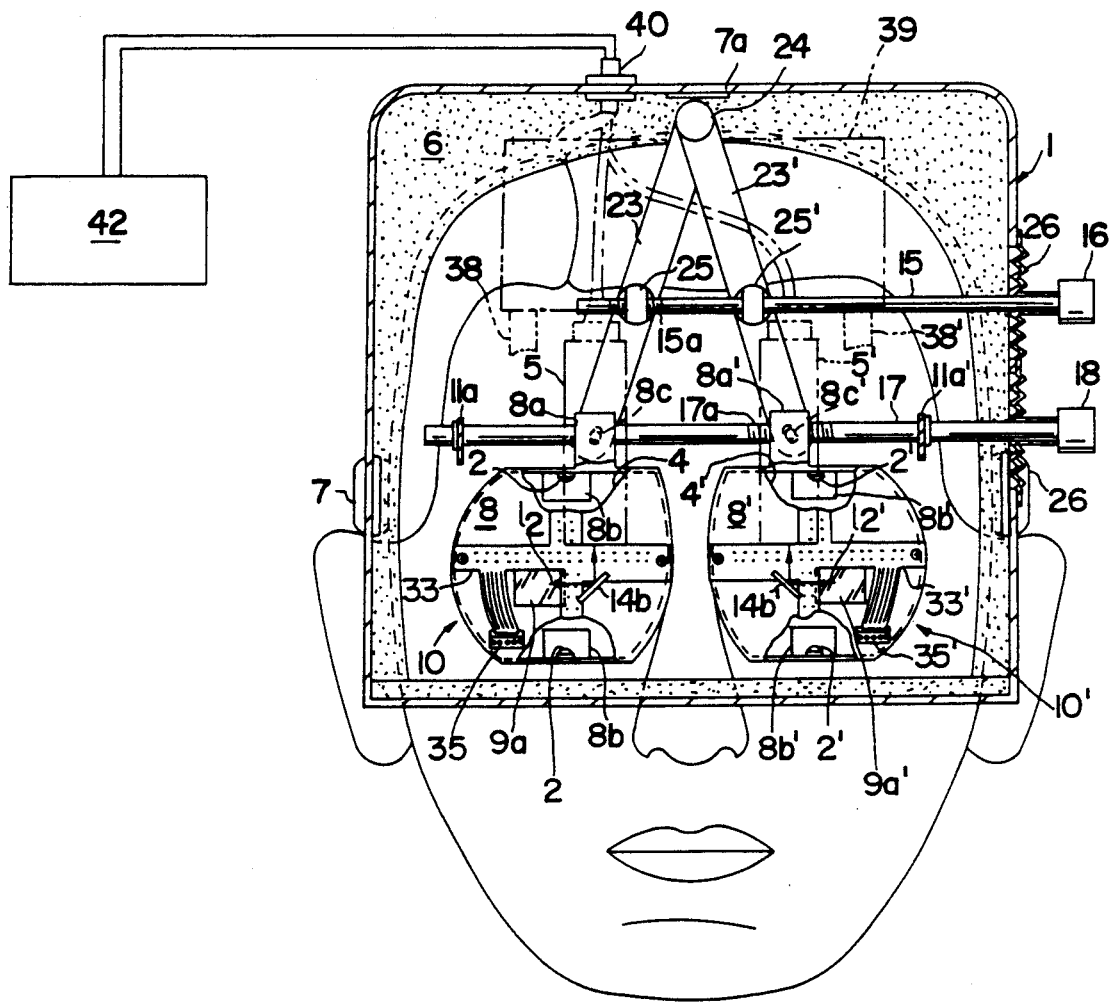
FIG. 2 is a cross sectional front view thereof taken along the line A—A of FIG. 1.
Figure 4:
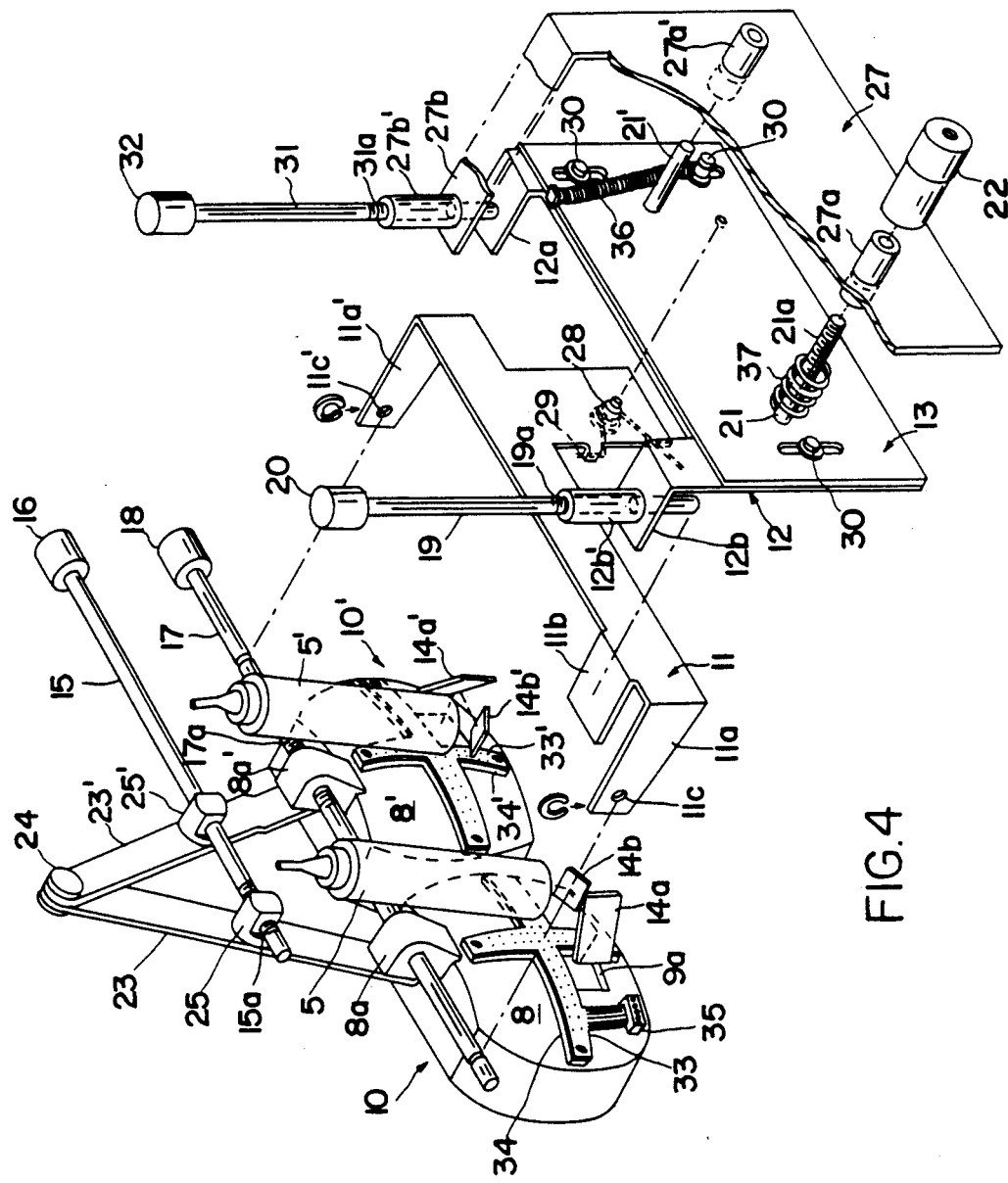
FIG. 4 is an exploded perspective view thereof.

Behind the two rectangular, transparent windows 9a and 9a', horizontal deflection mirrors 14a and 14a' are provided so that the optical paths of the eye infrared images from each eye face the pair of infrared ray detecting TV cameras 5 and 5' positioned vertically upward and slightly inward from the left and right ocular axes. In other words the optical axes 12 and 12' of the TV cameras 5 and 5' are set so that they face the eyeball. The optical paths thus deflected allow the light to enter the infrared ray detecting TV cameras 5 and 5' via the mirrors 14b and 14b' which deflect the light vertically upward (FIGS. 2, 3 and 4). The television cameras 5 and 5' employ fixed-focus lenses. In this way, the mobile eyepieces 10 and 10' can be made compact as a whole.

The LEDs 3 and 3' mounted on the flexible substrates 33 and 33' are caused to light via connector terminals 35 and 35' mounted on the back of the eye caps 8 and 8'. More the terminals at the ends of flexible cables 38 and 38' are connected to the connector terminals 35 and 35', and via the target controller 39 provided inside the goggles 1, the LED2 3 and 3' are operated by control signals from outside of the goggles.

On the upper frames of the pair of eye caps 8 and 8', guide blocks 8a and 8a' having guide holes which regulate the left and right movements of the eye caps 8 and 8' are provided. A horizontal axle 17, having a knob 18 at its one end and outside of the goggles 1, passes through the guide holes of the guide blocks 8a and 8a'. The left side guide block 8a is freely movable on the axle 17, and the right side guide block 8a' is threaded to a male thread 17a formed on the axle 17 so that the block 8a' is horizontally adjustable when the knob 18 is rotated. Both side blocks 8a and 8a' have pins 8c and 8c' embedded in the front side (patient's side), and the pins 8c and 8c' are freely and swingably connected to a pair of arms 23 and 23' through oblong holes formed at the lower ends thereof. The arms 23 and 23' are pivotable around a shaft 24 at their upper ends.

A pair of shaft supporting blocks 25 and 25' are rotatably mounted at the middle of the arms 23 and 23', and an eye-width adjustment shaft 15 passes through the supporting blocks 25 and 25'. The eye-width adjustment shaft 15 is used for changing the space between the arms 23 and 23', in other words, the distance between the eye caps 8 and 8' is widened or shortened so that the eye caps 8 and 8' can exactly match the eye width of the patient. The left side supporting block 25 threads with a male thread 15a formed on the eye-width adjustment shaft 15. The right side supporting block 25' is provided so that the shaft 15 can be freely rotatable therein at a fixed positional relationship to the right and left directions of the shaft 15. The space between the two supporting blocks 25 and 25' is adjusted via a knob 16 which is positioned outside of the goggle 1. In other words, by rotating the knob 16, the pair of arms 23 and 23' are opened and closed so that the distance between the eye caps 8 and 8' can be adjusted.

The horizontal adjustment shaft 17 is supported by a rotation frame 11 provided to allow rotation which is centered around a longitudinal axis (Z direction), in which the horizontal inclination (which is the inclination of the eye-width direction) can be changed. The shaft 17 is supported by a rotation frame support shaft 28 (FIG. 4) for free rotation embedded at a predetermined position of an elevation frame 12 located at the center of the multiple mobile frames 11, 12 and 13. The shaft 17 is thus supported by the support arms 11a and 11' on both left and right sides of the rotation frame 11 which is urged clockwise by a rotating spring 29, with the shaft 17 inserted through holes 11c and 11c' punched out the arms 11a and 11a' and stopped by a pair of E rings.

When an eye-width direction inclination adjustment shaft 19 having a male thread 19a threaded to a bushing 12b' provided on the upper left bent part 12b of the elevation frame 12 is rotated using the eye-width direction inclination adjustment knot 20 exposed to the outside of the goggles 1, the upper left bent part 11b of the rotation frame 11 is driven by the lower end of the adjustment shaft 19 to an allow inclination adjustment in the eye-width direction.

The elevation frame 12 is urged upward by tension spring 36 supported and guided by three guide pins 30 provided on the longitudinally (Z direction) movable frame 13. A support plate 27 is fixed inside the rear wall of the goggles 1 and has a bush 27b' on the bent part 27b at the upper right corner. The tip end of a vertical adjustment shaft 31, which is threaded to the male thread 31a of the bushing 27b', contacts the upper right bent part 12a of the elevation frame 12. Thus, when a knob 32, which adjusts the vertical positioning of the shaft 31 and projects out of the goggles 1, is rotated, the vertical position of the elevation frame 12 is adjusted.

The longitudinally movable frame 13 can move back and forth guided by a pair of longitudinal movement shafts 21 and 21' which are inserted into a pair of guide bushings 27a and 27a' provided on the support plate 27. Of the pair of longitudinal movement shafts 21 and 21', the shaft 21 which is on the left side and is longer than the other shaft 21' is formed with a male-thread section 21a at the end. The male-thread section 21a passes through the bushing 27a, and a longitudinal adjustment knob 22 having a female-thread section therein is screwed thereto. The front end of the knob 22 contacts the support plate 27, pressing a compression spring 37 fitted on the shaft 21. Thus, the longitudinally movable frame 13 can move back and forth when the knob 22 is turned.

At the sections where the eye-width adjustment shaft 15, horizontal adjustment shaft 17, eye-width directional inclination adjustment shaft 19, and vertical adjustment shaft 31 project through the outer wall of the goggles, multi-ringed, corrugated and flexible sheets 26 which shut out light are fitted around these adjustment shafts. The light-shutting sheets 26 are designed not to hinder the rotation of the knobs 16, 18, 20 and 32 and completely shut out the light even when the adjustment shafts 15, 17, 19 and 31 are rotated to make positional adjustments of the eye pieces 10 and 10'.

To test the patient's eye movements, first the patient's eye width is measured with a scale. Based upon the thus obtained dimension, the eyepieces 10 and 10' are set at the distance thus obtained so that the targets at the center of the target groups in the eyepiece parts 10 and 10' are equal to the eye width of the patient.

Next, the goggles 1 are placed on the patient's head, and both mobile eyepiece 10 and 10' are positioned so that they face toward the eyes. Then, air is supplied to the air band 7 from the air pump via operation of a computer (not shown). The air band 7 is inflated by compressed air and securely fastens the goggles 1 to the patient's head.

Electrical power is supplied via cables 40 to the infrared ray detecting TV cameras 5 and 5' and the infrared ray LEDs (IR-LEDs) in each eyepiece 10 and 10'. The infrared rays from the LEDs 2 and 2' are reflected and dispersed from the vertical plates 8b and 8b' of the eye caps 8 and 8' and by the reflection plates 4 and 4'. The light from the patient's eyes is evenly illuminated as the infrared rays passes through the cross-shaped transparent windows 9a and 9a' and enters the infrared ray detecting TV cameras 5 and 5' when the optical paths are deflected by the two mirrors.

The image signals from the TV cameras 5 and 5' are sent to the analyzer 42 via cable 40, and by the signals from the analyzer 42, images are displayed on a monitor (not shown).

Positional adjustment of the mobile eyepieces 10 and 10' are performed by observing the displayed images. In particular, adjustment of the right side mobile eyepiece 10' in the X, Y and Z directions is accomplished via adjustment knobs 18, 16 and 22 so that the left eye image of the patient is displayed at a predetermined location on the monitor. Then, the inclination of the eye-width direction is adjusted via the knob 20 to correctly display both eyes.

After this, adjustment of the eye pieces 10 and 10' are made to meet the individual positional differences in the patient's eyes. In particular, optical stimuli by the LED targets 3 and 3', depending upon intended tests, is given to the patient's eyes. In other words, LEDs of the targets 3 and 3' are turned on and off via the target controller 39 through control signals supplied from the analyzer 42 so that they look as if lighted LEDs moving vertically and horizontally. The patient's eyes follow the lighted LEDs and thus make eye movements, and such movements enter the cameras 5 and 5' as infrared images. Such images are then taken out by the cameras 5 and 5' which are sync-driven by sync signals from the analyzer 42 and sent to an image processor of the analyzer 42 and processed as intended therein and displayed on a monitor for visual inspection. The inspection results and other information obtained are recoded in recording devices.

The inspection device of the present invention is not limited to the embodiment described above and can be modified into a variety of different ways which are within the scope of the concept of the present invention.

As is clear from the above description, the present invention provides the following effects:

The shutter provided on the goggles matches the configuration of the patient's face and completely covers gaps between the goggles and the face thereby creating a "darkroom" in front of the patient's eyes. The patient is thus visually in "darkness", and since the goggles can move together with the patient, the testing room does not need to be a darkroom, visual fixation of the patient is eliminated, and the patient can move freely. Thus, with the infrared ray radiator for radiating light to the patient's eyes in the goggles and with the optical axes of the infrared ray detecting TV cameras positioned to face the patient's eyes, observation, recording, and measurement of free eye movement including cycloduction in a lighted room is performed via eye movement image signals. The infrared ray illumination provided by the present invention enables examination of eyes in darkness condition without subjecting the patient to a bright glare.

Effective illumination of the patient's eye by reflection plates for reflection and dispersion of infrared ray help image processing of the image signals from the infrared detecting television cameras.

The targets which are visible light sources are equipped with is the goggles and therefore a large (room) space is not required for the targets.

In addition, the infrared ray radiator, infrared ray detecting TV camera, targets, and reflection plates are provided in pairs inside the goggles so that they are positioned exactly in front of the right and left eyes of the patient; thus, observation of both eyes may be simultaneously accomplished.

When the goggles are mounted on the patient, the pair of mobile eyepieces, each incorporated with the infrared ray radiator, infrared ray detecting TV camera, targets, and reflection plate, are adjusted horizontally, vertically and in the ocular axis directions depending upon the patient's eyes with the optical-axis adjustment device. Thus, ocular axes and camera optical axes are accurately adjusted regardless of differences of the patient's eye positions, and comprehensive visual observation and accurate test results are obtained through monitors. In addition, since the targets and television cameras maintain a constant positional relationship, adjustment, observation and data corrections can be performed easily. Lastly, since the ocular axis direction can be adjusted, the distance between the mobile eyepieces and the eyes can be kept constant, eliminating visual angle corrections for the targets.

The fact that the infrared ray radiator is an infrared LEDs allows that they may be readily installed in the goggles and easily controlled.

The targets are multiple LEDs which emit visible light on and off as controlled, provided on the spherical surfaces, and centered on the center of eye movement, they are installed and controlled easily. Furthermore, the target positions require no correction for accurate eye movement observation.

Target LEDs are arranged in a cross (+) form, or vertically and horizontally, with the center target LED which is on the ocular axis and provided on a reflection plate having a spherical reflecting surface. Also, the optical axis of the television camera is set in the proximity of the center of the crossed targets and projects through the reflection plate. Accordingly, the light of LED which is the target for eye examination can be moved in horizontal and vertical directions to stimulate the eyes. Moreover, the positional relationship between the targets and television cameras can be set appropriately for conducting the tests.

Since the goggles are designed to be put on the patient via an air band, they are easily mounted and removed. Furthermore, the pressure of the air supplied to the air band is constant and the goggles may be placed on any patient despite individual differences.

We claim:

1. An eye movement inspection device comprising:
    goggles provided with an optical shutter which snugly fits on the head and face of a patient so as to prevent visible light from entering into the eyes of said patient and create a dark room in front of said eyes of said patient, said goggles being further provided with a head mounting means;
    an infrared ray radiating means provided in said goggles so as to irradiate said eyes of said patient;
    mobile eyepieces which are installed in said goggles and provided with infrared ray detecting television cameras and targets, said television cameras being for detecting and photographing infrared ray image of eye ball movement of said patient, and said targets being comprised of visible light sources which irradiate visible lights to said eyes of said patient;
    an optical-axis adjustment device which movably supports said mobile eyepieces, said adjustment device being controllable by operating means provided outside of said goggles so that said mobile eyepieces in said goggles are adjustable in three directions that comprises a horizontal direction which is a direction of a width of eyes, a vertical direction which crosses at right angles with the direction of the width of eyes and a direction of ocular axis so that optical axes of said television cameras are toward eye balls of said patient.

2. An eye movement inspection device within the scope of claim 1, wherein the infrared radiating means, infrared ray detecting television camera, reflection plate and targets are all provided in pairs so that each correspond to the left and right eyes of the patient.

3. An eye movement inspection device within the scope of claim 2, wherein a pair of mobile eyepieces corresponding to the left and right eyes of the patient are each formed by said infrared radiating means, infrared ray detecting television camera, reflection plates and targets as a unit, and while the optical axes of the television cameras face the eyes of the patient, said mobile eyepieces are adjusted via said optical-axis adjustment device horizontally in the direction of the eye width, vertically in the direction which crosses at right angles with the direction of width of the eyes and in the ocular axis direction relative to the patient's eyes.

4. An eye movement inspection device within the scope of any one of claims 2 or 3, wherein said targets consist of multiple visible light emitting diodes (LEDs) with display thereof changeable and are provided on a spherical surface centered at the center of eye movement.

5. An eye movement inspection device within the scope of claim 4, wherein the targets are provided in a cross shape vertically and horizontally from the intersection of targets on the ocular axes, hence on a reflection plate with a prescribed shape, the reflection surfaces being spherical surfaces, and wherein the optical axis of said television camera is positioned in proximity to said intersection targets and projecting through said reflection plate.

6. An eye movement inspection device according to claim 1, further comprising reflection plates provided in said goggles, said reflection plate reflecting and dispersing infrared rays and illuminating said eyes of said patient.

7. An eye movement inspection device within the scope of any one of claims 2, 3, 5, 1, or 6, wherein said head mounting means for said goggles is an air band.

8. An eye movement inspection device according to claim 2, 1 or 6, wherein each of said targets mounted on said movable eyepieces consists of a plurality of visible light emitting diodes which are turned on and off and arranged on a spherical plane centered at the center of eye movement.

9. An eye movement inspection device according to claim 8, wherein each of said targets mounted on said mobile eyepieces is provided on a reflection plate having a spherical reflection surface and said visible light emitting diodes are arranged in a cross shape so that a central diode which is at the center of said plurality of diodes arranged in a cross shape is positioned so as to be on an ocular axis, and each of said television cameras is provided so that optical axis thereof passes through said reflection plate provided near said central diode.

10. An eye movement inspection device according to claim 2, 1, or 6, wherein said optical axis adjustment device comprises horizontal, vertical and ocular axis direction adjustment means for adjusting said mobile eyepieces, one of said adjustment means being movable provided relatively to a side wall of said goggles and other adjustment means belong cooperatively and movably provided on said one adjustment means so that each of said adjustment means can be moved in each of said horizontal, vertical and ocular axis directions by operating means provided outside of said goggles.

11. An eye movement inspection device according to claim 2, 1, or 6, wherein said head mounting means is an air band.

* * * * *